United States Patent
Sand et al.

(10) Patent No.: US 9,657,109 B2
(45) Date of Patent: May 23, 2017

(54) COMPOSITIONS AND METHODS FOR THE TREATMENT OF SYSTEMIC INFLAMMATORY RESPONSE SYNDROMES

(71) Applicant: Wisconsin Alumni Research Foundation, Madison, WI (US)

(72) Inventors: Jordan Marshall Sand, Madison, WI (US); Mark Eric Cook, Madison, WI (US); Daniel Elmer Butz, Madison, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 1149 days.

(21) Appl. No.: 13/667,346

(22) Filed: Nov. 2, 2012

(65) Prior Publication Data
US 2014/0127190 A1 May 8, 2014

(51) Int. Cl.
| | |
|---|---|
| A61K 39/395 | (2006.01) |
| C07K 16/40 | (2006.01) |
| C12N 9/20 | (2006.01) |
| C07K 5/113 | (2006.01) |
| A61K 39/00 | (2006.01) |

(52) U.S. Cl.
CPC ............ C07K 16/40 (2013.01); C07K 5/1021 (2013.01); C12N 9/20 (2013.01); C12Y 301/01004 (2013.01); A61K 2039/505 (2013.01); C07K 2317/11 (2013.01); C07K 2317/23 (2013.01); C07K 2317/76 (2013.01)

(58) Field of Classification Search
None
See application file for complete search history.

(56) References Cited

U.S. PATENT DOCUMENTS

| | | |
|---|---|---|
| 6,213,930 B1 | 4/2001 | Cook |
| 6,383,485 B1 | 5/2002 | Cook |
| 7,579,156 B2 | 8/2009 | Tsao et al. |
| 2007/0298022 A1 | 12/2007 | Scherer et al. |
| 2012/0122117 A1 | 5/2012 | Lee et al. |

FOREIGN PATENT DOCUMENTS

| | | | |
|---|---|---|---|
| CN | WO 2013143026 A1 * | 10/2013 | ........... C07K 16/005 |
| WO | 9856400 A1 | 12/1998 | |
| WO | 0054604 A1 | 9/2000 | |
| WO | 2010094011 A1 | 8/2010 | |
| WO | 2011051527 A1 | 5/2011 | |
| WO | 2013143504 A1 | 10/2013 | |

OTHER PUBLICATIONS

Tamaru et al.; "Deficiency of Phospholipase A2 Receptor Exacerbates Ovalbumin-Induced Lung Inflammation"; J. Immunol; 191(3); pp. 1021-1028; (2013).
International Search Report and Written Opinion: International Application No. PCT/US2013/067006; International Filing Date Oct. 28, 2013; Date of Mailing Dec. 12, 2013; 12 pages.
Berlot et al.; "Use of IgM and IgA-enriched Immunoglobulins in the Treatment of Severe Sepsis and Septic Shock"; Minerva Anestesiol; 70; pp. 739-745; (2004).
DeMaio et al.; "Genetic Component in the Inflammatory Response Induced by Bacterial Lipopolysaccharide"; Shock; 10(5); pp. 319-323; (1998).
Eerola et al.; "Analysis of Expression of Secreted Phospholipases A2 in Mouse Tissues at Protein and mRNA levels"; Bochimica et Biophysica Acta; 1761; pp. 745-756; (2006).
Hanasaki et al.; "Resistance to Endotoxic Shock in Phospholipase A2 Receptor-deficient Mice"; The Journal of Biological Chemistry; 272(52); pp. 32792-32797; (1997).
Kennedy, et al.; "A Natural Disruption of the Secretory Group II Phospholipase A2 Gene in Inbred Mouse Strains"; The Journal of Biological Chemistry; 270(38); pp. 22378-22385; (1995).
Marschan et al.; "Probiotics in Infancy Induce Protective Immune Profiles that are Characteristic for Chronic Los-Grade Inflammation"; Clinical and Experimental Allergy; 38; pp. 611-618; (2008).
Pierce et al.; "Effects of Spray-Dried animal Plasma and Immunoglobulins on Performance of Early Weaned Pigs"; Journal of Animal Science; 83; pp. 2876-2885; (2005).
Yokota et al.; "Enhanced Tissue Expression and Elevated Circulating Level of Phospholipase A2 Receptor During Murine Endotoxic Shock"; Archives of Biochemistry and Biophysics; 379(1); pp. 7-17; (2000).
Yokota et al.; "Suppression of Murine Endotoxic Shock by sPLA2 Inhibitor, Indoxam, Through Group IIA sPLA2-Independent Mechanisms"; Biochimica et Biophysica Acta; 1438; pp. 213-222; (1999).
Zayat et al.; "Pathophysiology of LPS-Induced Gastrointestinal Injury in the Rat: Role of Secretory Phospholipase A2"; Shock; 30(2) pp. 206-211; (2008).
Zeiher et al.; "LY315920NA/S-5920, a selective inhibitor of group IIA secretory phospholipase A2, fails to improve clinical outcome for patients with severe sepsis*"; Crit Care Med; 33(8); pp. 1741-1748; (2005).

* cited by examiner

Primary Examiner — Sharon Wen
(74) Attorney, Agent, or Firm — Cantor Colburn LLP

(57) ABSTRACT

Described herein are peptides from secretory phospholipase $A_2$-IB and antibodies that can be used to reduce the contribution of the gastrointestinal tract to inflammatory processes including systemic inflammatory responses. Specifically, antibodies that bind specifically a peptide from secretory phospholipase $A_2$-IB prevent death in a mouse model of LPS-induced endotoxemia. The antibodies described herein are particularly useful to treat systemic inflammatory response syndromes, including sepsis.

10 Claims, 3 Drawing Sheets

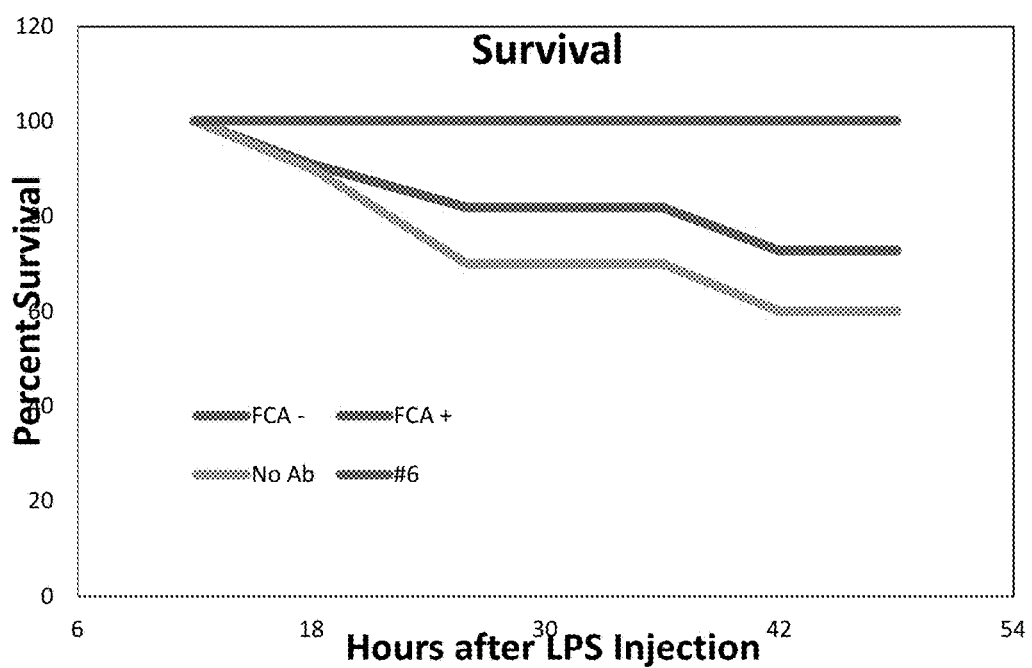

SEQUENCE LISTING

```
<160> NUMBER OF SEQ ID NOS: 22

<210> SEQ ID NO 1
<211> LENGTH: 8
<212> TYPE: PRT
<213> ORGANISM: Mus musculus

<400> SEQUENCE: 1

Val Pro Tyr Asn Lys Glu Tyr Lys
1               5

<210> SEQ ID NO 2
<211> LENGTH: 8
<212> TYPE: PRT
<213> ORGANISM: Homo sapiens

<400> SEQUENCE: 2

Ala Pro Tyr Asn Lys Ala His Lys
1               5

<210> SEQ ID NO 3
<211> LENGTH: 8
<212> TYPE: PRT
<213> ORGANISM: Sus scrofa

<400> SEQUENCE: 3

Ala Pro Tyr Asn Lys Glu His Lys
1               5

<210> SEQ ID NO 4
<211> LENGTH: 8
<212> TYPE: PRT
<213> ORGANISM: rabbit

<400> SEQUENCE: 4

Arg Pro Tyr Asn Lys Glu Tyr Lys
1               5

<210> SEQ ID NO 5
<211> LENGTH: 8
<212> TYPE: PRT
<213> ORGANISM: bovine

<400> SEQUENCE: 5

Val Pro Tyr Asn Lys Glu His Lys
1               5

<210> SEQ ID NO 6
<211> LENGTH: 8
<212> TYPE: PRT
<213> ORGANISM: Artificial Sequence
<220> FEATURE:
```

```
<223> OTHER INFORMATION: Consensus sequence
<220> FEATURE:
<221> NAME/KEY: X
<222> LOCATION: (1)..(1)
<223> OTHER INFORMATION: V or A or R
<220> FEATURE:
<221> NAME/KEY: X
<222> LOCATION: (6)..(6)
<223> OTHER INFORMATION: A or E
<220> FEATURE:
<221> NAME/KEY: X
<222> LOCATION: (7)..(7)
<223> OTHER INFORMATION: H or Y

<400> SEQUENCE: 6

Xaa Pro Tyr Asn Lys Xaa Xaa Lys
1               5

<210> SEQ ID NO 7
<211> LENGTH: 4
<212> TYPE: PRT
<213> ORGANISM: Artificial Sequence
<220> FEATURE:
<223> OTHER INFORMATION: Consensus

<400> SEQUENCE: 7

Pro Tyr Asn Lys
1

<210> SEQ ID NO 8
<211> LENGTH: 146
<212> TYPE: PRT
<213> ORGANISM: Mus musculus

<400> SEQUENCE: 8

Met Lys Leu Leu Leu Leu Ala Ala Leu Leu Thr Ala Gly Ala Ala Ala
1               5                   10                  15

His Ser Ile Ser Pro Arg Ala Val Trp Gln Phe Arg Asn Met Ile Lys
                20                  25                  30

Cys Thr Ile Pro Gly Ser Asp Pro Leu Lys Asp Tyr Asn Asn Tyr Gly
            35                  40                  45

Cys Tyr Cys Gly Leu Gly Gly Trp Gly Thr Pro Val Asp Asp Leu Asp
        50                  55                  60

Arg Cys Cys Gln Thr His Asp His Cys Tyr Ser Gln Ala Lys Lys Leu
65                  70                  75                  80

Glu Ser Cys Lys Phe Leu Ile Asp Asn Pro Tyr Thr Asn Thr Tyr Ser
                85                  90                  95

Tyr Ser Cys Ser Gly Ser Glu Ile Thr Cys Ser Ala Lys Asn Asn Lys
            100                 105                 110

Cys Glu Asp Phe Ile Cys Asn Cys Asp Arg Glu Ala Ala Ile Cys Phe
        115                 120                 125

Ser Lys Val Pro Tyr Asn Lys Glu Tyr Lys Asn Leu Asp Thr Gly Lys
130                 135                 140

Phe Cys
145

<210> SEQ ID NO 9
<211> LENGTH: 148
<212> TYPE: PRT
<213> ORGANISM: Homo sapiens

<400> SEQUENCE: 9

Met Lys Leu Leu Val Leu Ala Val Leu Leu Thr Val Ala Ala Ala Asp
```

```
1               5                   10                  15
Ser Gly Ile Ser Pro Arg Ala Val Trp Gln Phe Arg Lys Met Ile Lys
                20                  25                  30

Cys Val Ile Pro Gly Ser Asp Pro Phe Leu Glu Tyr Asn Asn Tyr Gly
                35                  40                  45

Cys Tyr Cys Gly Leu Gly Gly Ser Gly Thr Pro Val Asp Glu Leu Asp
                50                  55                  60

Lys Cys Cys Gln Thr His Asp Asn Cys Tyr Asp Gln Ala Lys Lys Leu
 65                 70                  75                  80

Asp Ser Cys Lys Phe Leu Leu Asp Asn Pro Tyr Thr His Thr Tyr Ser
                85                  90                  95

Tyr Ser Cys Ser Gly Ser Ala Ile Thr Cys Ser Ser Lys Asn Lys Glu
               100                 105                 110

Cys Glu Ala Phe Ile Cys Asn Cys Asp Arg Asn Ala Ala Ile Cys Phe
               115                 120                 125

Ser Lys Ala Pro Tyr Asn Lys Ala His Lys Asn Leu Asp Thr Lys Lys
           130                 135                 140

Tyr Cys Gln Ser
145
```

<210> SEQ ID NO 10
<211> LENGTH: 146
<212> TYPE: PRT
<213> ORGANISM: Sus scrofa

<400> SEQUENCE: 10

```
Met Lys Phe Leu Val Leu Ala Val Leu Leu Thr Val Gly Ala Ala Gln
 1               5                   10                  15

Glu Gly Ile Ser Ser Arg Ala Leu Trp Gln Phe Arg Ser Met Ile Lys
                20                  25                  30

Cys Ala Ile Pro Gly Ser His Pro Leu Met Asp Phe Asn Asn Tyr Gly
                35                  40                  45

Cys Tyr Cys Gly Leu Gly Gly Ser Gly Thr Pro Val Asp Glu Leu Asp
                50                  55                  60

Arg Cys Cys Glu Thr His Asp Asn Cys Tyr Arg Asp Ala Lys Asn Leu
 65                 70                  75                  80

Asp Ser Cys Lys Phe Leu Val Asp Asn Pro Tyr Thr Glu Ser Tyr Ser
                85                  90                  95

Tyr Ser Cys Ser Asn Thr Glu Ile Thr Cys Asn Ser Lys Asn Asn Ala
               100                 105                 110

Cys Glu Ala Phe Ile Cys Asn Cys Asp Arg Asn Ala Ala Ile Cys Phe
               115                 120                 125

Ser Lys Ala Pro Tyr Asn Lys Glu His Lys Asn Leu Asp Thr Lys Lys
           130                 135                 140

Tyr Cys
145
```

<210> SEQ ID NO 11
<211> LENGTH: 144
<212> TYPE: PRT
<213> ORGANISM: rabbit

<400> SEQUENCE: 11

```
Met Lys Phe Leu Val Leu Ala Ala Leu Leu Thr Ala Gly Thr Ala Ala
 1               5                   10                  15

Ser Gly Val Ser Pro Thr Ala Leu Trp Gln Phe Arg Gly Met Ile Gln
```

```
            20                  25                  30
Cys Thr Ile Pro Gly Ser Ser Pro Tyr Leu Glu Phe Asn Gly Tyr Gly
            35                  40                  45

Cys Tyr Cys Gly Leu Gly Gly Ser Gly Thr Pro Val Asp Glu Leu Asp
            50                  55                  60

Arg Cys Cys Gln Thr His Asp Gln Cys Tyr Thr Gln Ala Lys Lys Leu
65                  70                  75                  80

Ser Ser Cys Ser Phe Leu Val Asp Asn Pro Tyr Thr Asn Ser Tyr Ser
                85                  90                  95

Tyr Ser Cys Ser Gly Thr Thr Val Thr Cys Ser Ser Lys Asn Lys Glu
            100                 105                 110

Cys Glu Ala Phe Ile Cys Asp Cys Asp Arg Lys Ala Ala Ile Cys Phe
            115                 120                 125

Ser Lys Arg Pro Tyr Asn Lys Glu Tyr Lys Pro Ile Ser Lys Tyr Cys
            130                 135                 140

<210> SEQ ID NO 12
<211> LENGTH: 145
<212> TYPE: PRT
<213> ORGANISM: bovine

<400> SEQUENCE: 12

Met Arg Leu Leu Val Leu Ala Ala Leu Leu Thr Val Gly Ala Gly Gln
1               5                   10                  15

Ala Gly Leu Asn Ser Arg Ala Leu Trp Gln Phe Asn Gly Met Ile Lys
            20                  25                  30

Cys Lys Ile Pro Ser Ser Glu Pro Leu Leu Asp Phe Asn Asn Tyr Gly
            35                  40                  45

Cys Tyr Cys Gly Leu Gly Gly Ser Gly Thr Pro Val Asp Asp Leu Asp
            50                  55                  60

Arg Cys Cys Gln Thr His Asp Asn Cys Tyr Lys Gln Ala Lys Lys Leu
65                  70                  75                  80

Asp Ser Cys Lys Val Leu Val Asp Asn Pro Tyr Thr Asn Asn Tyr Ser
                85                  90                  95

Tyr Ser Cys Ser Asn Asn Glu Ile Thr Cys Ser Ser Glu Asn Asn Ala
            100                 105                 110

Cys Glu Ala Phe Ile Cys Asn Cys Asp Arg Asn Ala Ala Ile Cys Phe
            115                 120                 125

Ser Lys Val Pro Tyr Asn Lys Glu His Lys Asn Leu Asp Lys Lys Asn
            130                 135                 140

Cys
145

<210> SEQ ID NO 13
<211> LENGTH: 146
<212> TYPE: PRT
<213> ORGANISM: canine

<400> SEQUENCE: 13

Met Lys Phe Leu Val Leu Ala Ala Leu Leu Thr Val Ala Ala Ala Glu
1               5                   10                  15

Gly Gly Ile Ser Pro Arg Ala Val Trp Gln Phe Arg Asn Met Ile Lys
            20                  25                  30

Cys Thr Ile Pro Glu Ser Asp Pro Leu Lys Asp Tyr Asn Asp Tyr Gly
            35                  40                  45

Cys Tyr Cys Gly Leu Gly Gly Ser Gly Thr Pro Val Asp Glu Leu Asp
```

```
                50                  55                  60
Lys Cys Cys Gln Thr His Asp His Cys Tyr Ser Glu Ala Lys Lys Leu
 65                  70                  75                  80

Asp Ser Cys Lys Phe Leu Leu Asp Asn Pro Tyr Thr Lys Ile Tyr Ser
                 85                  90                  95

Tyr Ser Cys Ser Gly Ser Glu Ile Thr Cys Ser Ser Lys Asn Lys Asp
            100                 105                 110

Cys Gln Ala Phe Ile Cys Asn Cys Asp Arg Ser Ala Ala Ile Cys Phe
        115                 120                 125

Ser Lys Ala Pro Tyr Asn Lys Glu His Lys Asn Leu Asp Thr Lys Lys
    130                 135                 140

Tyr Cys
145

<210> SEQ ID NO 14
<211> LENGTH: 8
<212> TYPE: PRT
<213> ORGANISM: Mus musculus

<400> SEQUENCE: 14

Gly Gly Trp Gly Thr Pro Val Asp
 1               5

<210> SEQ ID NO 15
<211> LENGTH: 8
<212> TYPE: PRT
<213> ORGANISM: Mus musculus

<400> SEQUENCE: 15

Pro Gly Ser Asp Pro Leu Lys Asp
 1               5

<210> SEQ ID NO 16
<211> LENGTH: 8
<212> TYPE: PRT
<213> ORGANISM: Mus musculus

<400> SEQUENCE: 16

Lys Asp Tyr Asn Asn Tyr Gly Cys
 1               5

<210> SEQ ID NO 17
<211> LENGTH: 8
<212> TYPE: PRT
<213> ORGANISM: Mus musculus

<400> SEQUENCE: 17

Asn Asn Tyr Gly Cys Tyr Cys Gly
 1               5

<210> SEQ ID NO 18
<211> LENGTH: 8
<212> TYPE: PRT
<213> ORGANISM: Mus musculus

<400> SEQUENCE: 18

Ala Ala His Ser Ile Ser Pro Arg
 1               5

<210> SEQ ID NO 19
<211> LENGTH: 8
<212> TYPE: PRT
```

```
<213> ORGANISM: Mus musculus

<400> SEQUENCE: 19

Lys Glu Tyr Lys Asn Leu Asp Thr
1               5

<210> SEQ ID NO 20
<211> LENGTH: 8
<212> TYPE: PRT
<213> ORGANISM: Mus musculus

<400> SEQUENCE: 20

Thr Tyr Ser Tyr Ser Cys Ser Gly
1               5

<210> SEQ ID NO 21
<211> LENGTH: 8
<212> TYPE: PRT
<213> ORGANISM: Mus musculus

<400> SEQUENCE: 21

Gly Cys Tyr Cys Gly Leu Gly Gly
1               5

<210> SEQ ID NO 22
<211> LENGTH: 8
<212> TYPE: PRT
<213> ORGANISM: Mus musculus

<400> SEQUENCE: 22

Cys Phe Ser Lys Val Pro Tyr Asn
1               5
```

COMPOSITIONS AND METHODS FOR THE TREATMENT OF SYSTEMIC INFLAMMATORY RESPONSE SYNDROMES

FIELD OF THE DISCLOSURE

The present disclosure is related to compositions of matter, including peptides and antibodies that reduce the contribution of the gastrointestinal tract to inflammatory processes including systemic inflammatory responses. Methods of using the compositions to treat systemic inflammatory response syndromes are also included.

BACKGROUND

Systemic inflammatory response syndromes are characterized by an excessive and dysregulated inflammatory response in the host, often triggered by an interaction between a pathogenic microorganism and a host's defense system. Animals and humans that undergo surgical procedures or hospitalization under intensive, e.g., ventilated care, have an increased risk of infectious systemic inflammatory response syndrome that can culminate into septic shock, multiple organ dysfunction, and finally death. Sepsis is a systemic inflammatory response syndrome with a confirmed infection. Septic shock is sepsis-induced hypotension that is resistant to fluid resuscitation with the additional presence of hypoperfusion abnormalities. Improved treatments are essential to preventing the progression of systemic inflammatory response syndrome to sepsis and septic shock.

Current treatments for sepsis focus on elimination of infection (e.g., antibiotics) and treatments that stabilize the patient to established physiological parameters (e.g., fluid replacement for hypotension, NSAIDS for fever).

What is needed are alternative and adjunct therapies for the treatment of systemic inflammatory response syndromes, including sepsis.

BRIEF SUMMARY

In one aspect, a method of reducing the contribution of the gastrointestinal tract to an inflammatory process comprises orally administering to an individual in need thereof an inhibitor of secretory phospholipase $A_2$-IB. In specific embodiments, the inhibitor is an antibody.

In another aspect, a method of making an antibody that specifically binds secretory phospholipase $A_2$-IB comprises immunizing an animal with a peptide comprising at least four contiguous amino acids of (V/A/R)PYNK(A/E)(H/Y)K (SEQ ID NO. 6), wherein the at least four contiguous amino acids include PYNK (SEQ ID NO. 7), wherein the peptide is not a full-length secretory phospholipase $A_2$-IB protein; and isolating the antibodies that specifically bind at least four contiguous amino acids of (V/A/R)PYNK(A/E)(H/Y)K (SEQ ID NO. 6), wherein the at least four contiguous amino acids include PYNK (SEQ ID NO. 7).

In yet another aspect, an isolated antibody specifically binds secretory phospholipase $A_2$-IB, wherein the isolated antibody specifically binds at least four contiguous amino acids of (V/A/R)PYNK(A/E)(H/Y)K (SEQ ID NO. 6), wherein the at least four contiguous amino acids include PYNK (SEQ ID NO. 7).

In a yet further aspect, included herein is an isolated peptide comprising 4 to 38 contiguous amino acid residues of a secretory phospholipase $A_2$-IB protein, wherein the peptide includes at least four contiguous amino acids of (V/A/R)PYNK(A/E)(H/Y)K (SEQ ID NO. 6), wherein the at least four contiguous amino acids include PYNK (SEQ ID NO. 7).

BRIEF DESCRIPTION OF THE DRAWINGS

FIG. 5 shows that anti-sPLA$_2$-IB peptide #6 (SEQ ID NO. 1) antibody is completely protective against LPS-induced sepsis mortality. Male Balb/c mice (10/group) were divided randomly and gavaged (100 ul) with either FCA, no antibody (no antibody), or peptide #6 antibody contained in a 10% egg yolk powder solution at the time of 10 mg/kg LPS injection and once every 24 hours thereafter. Mice were monitored until all mice showed signs of recovery from LPS injection.

Figure 1:
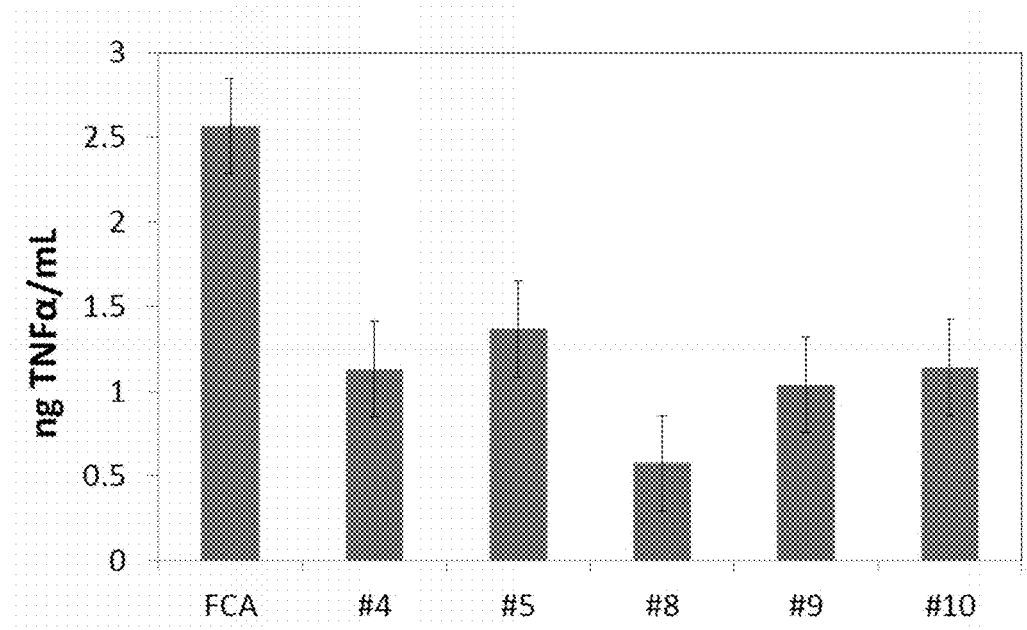
FIG. 1 shows that TNFα levels are decreased with certain anti-sPLA$_2$-IB antibodies. In this experiment, RAW 264.7 macrophages were plated and cultured (48 h) to 70% confluence in a 12-well plate. Egg yolk powder containing antibodies to anti-sPLA$_2$-IB peptides #4, 5, 8, 9, 10 (SEQ ID NOs. 17, 18, 20, 21 and 22) were then added to the plates in growth media at a dilution of 1:100 and allowed to incubate with the plate for 2 hours. 100 ng/well of lipopolysaccharide (LPS) was then added for 2 hours and the supernatant was collected. Representative of 3 replicates. Antibody to peptides #4, #5, #8, #9, and #10 reduced TNFα levels when compared to the FCA control (P<0.05 using a one way ANOVA).

The above-described and other features will be appreciated and understood by those skilled in the art from the following detailed description, drawings, and appended claims.

DETAILED DESCRIPTION

Preclinical animal trials have recently demonstrated that a possible factor in controlling the progression of sepsis to septic shock and death is through the regulation of host inflammation. The inventors of the present application have particularly identified gastrointestinal tract, e.g., mucosal, inflammation as a key factor in systemic inflammatory response syndromes. A systemic inflammatory response syndrome can occur in patients without the presence of infection, for example in those with burns, polytrauma, or the initial state in pancreatitis and chemical pneumonitis. Systemic inflammatory response syndromes are often triggered by a microorganism, and include sepsis where there is a confirmed infection. The intestinal contribution to shock is supported by resistance of germ-free animals to septic shock. Thus, based on the results presented herein, control of gastrointestinal tract inflammation and/or microbial translocation through the intestinal tract can be used to prevent the progression of systemic inflammatory response syndrome to sepsis to septic shock to death.

Phospholiase A2s ($PLA_2$) are enzymes that hydrolyze the sn-2 fatty acyl bond of phospholipids, producing free fatty acids and lysophospholipids. Three types of $PLA_2$ have been found in mammalian tissues, the secretory $PLA_2$, the cytosolic $PLA_2$, and the calcium-independent $PLA_2$. At least ten secretory $PLA_2$ ($sPLA_2$) isoforms have been identified in humans and these enzymes have molecular weights around 14 kDa. Among these proteins, the $sPLA_2$-IB and $sPLA_2$-IIA enzymes have been most extensively studied. $sPLA_2$-IIA is a non-pancreatic enzyme and has been found to correlate with local and systemic inflammatory responses. This enzyme is present in platelets and inflammatory cells including neutrophils and has been found in circulating blood and rheumatoid arthritis synovial fluid. $sPLA_2$-IIA inhibition has been suggested as a strategy to protect the gastrointestinal tract in a lipopolysaccharide (LPS)-induced gastrointestinal injury model. $sPLA_2$-IB, in contrast to $sPLA_2$-IIA, is generally considered as a pancreatic enzyme whose function mainly involves digestion of dietary phospholipids.

Instead of $PLA_2$-IIA, the inventors of the present application found that inhibitors of secretory phospholipase $A_2$-IB ($sPLA_2$-IB) can be used to inhibit the contribution of the gastrointestinal tract to an inflammatory process such as systemic inflammatory responses. In previous work from U.S. Pat. Nos. 6,383,485 and 6,213,930, a decrease in mortality and an increase in growth promotion were demonstrated using antibodies to $sPLA_2$. Because pigs do not express $sPLA_2$-IIA, the present inventors hypothesized that the effects are due to $sPLA_2$-IB. Other evidence from mice demonstrated a frame-shift mutation in the $sPLA_2$-IIA gene in mice that still were susceptible to sepsis. This along with further confirmation that knocking out the $sPLA_2$-IB receptor was protective against LPS-induced sepsis demonstrated that $sPLA_2$-IB was more important in sepsis than $sPLA_2$-IIA.

Included herein are isolated peptides that correspond to an isolated fragment of sPLA2-IB. Exemplary peptides include:

| Peptide | Organism | SEQ ID NO. |
|---|---|---|
| VPYNKEYK | mouse | SEQ ID NO. 1 |
| APYNKAHK | human | SEQ ID NO. 2 |
| APYNKEHK | pig, dog | SEQ ID NO. 3 |
| RPYNKEYK | rabbit | SEQ ID NO. 4 |
| VPYNKEHK | cow | SEQ ID NO. 5 |
| (V/A/R)PYNK(A/E)(H/Y)K | consensus | SEQ ID NO. 6 |

Also included herein are peptides smaller than SEQ ID NOs. 1-6 that correspond to isolated fragments of sPLA2-IB, such as PYNK (SEQ ID NO. 7). In one embodiment, an isolated peptide comprises at least four contiguous amino acids of (V/A/R)PYNK(A/E)(H/Y)K, wherein the at least four contiguous amino acids comprise PYNK. In other embodiments, the peptide comprises 5, 6, 7 or 8 amino acids of SEQ ID NO. 6.

The sequence of mouse $sPLA_2$-IB is accession number NP_035237.1 (SEQ ID NO. 8), human $sPLA_2$-IB is accession number NM_000928.2 (SEQ ID NO. 9), pig $sPLA_2$-IB is accession number NM_001004037.1 (SEQ ID NO. 10), rabbit $sPLA_2$-IB is accession number Q7M334 (SEQ ID NO. 11), cow $sPLA_2$-IB is accession number P00593 (SEQ ID NO. 12), and dog $sPLA_2$-IB is accession number P06596 (SEQ ID NO. 13).

Included herein is an isolated peptide comprising 4 to 38 contiguous amino acid residues of a secretory phospholipase $A_2$-IB protein, wherein the peptide includes at least four contiguous amino acids of (V/A/R)PYNK(A/E)(H/Y)K (SEQ ID NO. 6), wherein the at least four contiguous amino acids include PYNK (SEQ ID NO. 7). In a specific embodiment, the peptide comprises 6 to 38 contiguous amino acid residues of a secretory phospholipase $A_2$-IB protein, wherein the peptide includes at least four contiguous amino acids of (V/A/R)PYNK(A/E)(H/Y)K (SEQ ID NO. 6), wherein the at least four contiguous amino acids include PYNK (SEQ ID NO. 7). Also included herein is an isolated peptide comprising any one of SEQ ID NOs. 1-6. In specific embodiments, the peptide is not a full-length $sPLA_2$-IB protein. In specific embodiments, the peptide contains 4 to 38, 6 to 38, 8 to 30, 8 to 20, 8 to 15, 8 to 10, or 8 amino acid residues. For example, a peptide that contains SEQ ID NO. 1 may contain 6 to 38 contiguous amino acid residues of SEQ ID NO. 7. Similarly, a peptide that contains SEQ ID NO. 2 may contain 6 to 38 contiguous amino acid residues of SEQ ID NO. 8.

The isolated $sPLA_2$-IB peptides identified herein are particularly useful the design/production of inhibitors of $sPLA_2$-IB. In one embodiment, the peptide is employed in the production of antibodies that specifically bind $sPLA_2$-IB.

In a specific embodiment, an inhibitor of secretory phospholipase $A_2$-IB is an isolated antibody that specifically binds at least a portion of secretory phospholipase $A_2$-IB. The term antibody includes, for example, polyclonal and monoclonal antibodies as well as avian egg yolk antibodies. In a specific embodiment, disclosed herein is an isolated antibody that specifically binds a peptide from secretory phospholipase $A_2$-IB, wherein the peptide comprises at least four contiguous amino acids of any one of SEQ ID NOs. 1-6, wherein the at least four contiguous amino acids include PYNK (SEQ ID NO. 7). In other embodiments, the peptide comprising PYNK comprises 5, 6, 7 or 8 amino acids of any one of SEQ ID NOs. 1-6. In a specific embodiment, the isolated antibody specifically binds a $sPLA_2$-IB peptide consisting of any one of SEQ ID NOs. 1-6.

In one embodiment, an isolated antibody is produced by immunizing an animal with a peptide comprising a $sPLA_2$-IB peptide comprising at least four contiguous amino acids of any one of SEQ ID NOs. 1-6, wherein the at least four contiguous amino acids include PYNK (SEQ ID NO. 7). In one embodiment the peptide is not a full-length $sPLA_2$-IB peptide, such as a peptide containing 4 to 38 amino acids. Methods for preparing polyclonal and monoclonal antibodies are well known in the art. Polyclonal antibodies can be generated from a variety of warm-blooded animals such as horses, cows, goats, sheep, dogs, cats, pigs, mules, chickens, rabbits, mice, and rats. Polyclonal antibodies can be raised in a mammal, for example, by one or more injections of a $sPLA_2$-IB peptide and, if desired, an adjuvant. The $sPLA_2$-

IB peptide and/or adjuvant may be injected in the mammal by multiple subcutaneous or intraperitoneal injections. Examples of adjuvants which may be employed include Freund's complete adjuvant and MPL-TDM adjuvant (monophosphoryl Lipid A, synthetic trehalose dicorynomycolate). It may be useful to conjugate the sPLA$_2$-IB peptide to a protein known to be immunogenic in the mammal being immunized. Examples of such immunogenic proteins include but are not limited to keyhole limpet hemocyanin, serum albumin, bovine gamma globulin, bovine thyroglobulin, and soybean trypsin inhibitor. The immunization protocol may be selected by one skilled in the art without undue experimentation.

In one embodiment, a polyclonal antibody is isolated from the colostrum of a cow, sheep or goat immunized with a sPLA$_2$-IB peptide as described herein. Colostrum may be collected from immunized animals and antibodies isolated from the colostrum.

Monoclonal antibodies may be prepared using hybridoma methods. In a hybridoma method, a mouse, hamster, or other appropriate host animal, is immunized with a sPLA$_2$-IB peptide to elicit lymphocytes that produce or are capable of producing antibodies that will specifically bind to the sPLA$_2$-IB peptide. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. Immortalized cell lines are usually transformed mammalian cells, particularly myeloma cells of rodent, bovine and human origin. In specific embodiments, rat or mouse myeloma cell lines are employed. The hybridoma cells may be cultured in a suitable culture medium that contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Specific immortalized cell lines are those that fuse efficiently, support stable high level expression of antibody by the selected antibody-producing cells, and are sensitive to a medium such as HAT medium. More specific immortalized cell lines are murine myeloma lines. After the desired hybridoma cells are identified, the clones may be subcloned by dilution procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxyapatite chromatography, gel electrophoresis, dialysis, or affinity chromatography.

The monoclonal antibodies may also be made by recombinant DNA methods.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In another embodiment, the antibodies are humanized antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed by substituting rodent CDRs or CDR sequences for the corresponding sequences of a human antibody. Accordingly, such humanized antibodies are chimeric antibodies, wherein substantially less than an intact human variable domain has been substituted by the corresponding sequence from a non-human species. In practice, humanized antibodies are human antibodies in which some CDR residues and possibly some FR residues are substituted by residues from analogous sites in rodent antibodies.

Human antibodies can also be produced using various techniques known in the art, including phage display libraries. Similarly, human antibodies can be made by introducing human immunoglobulin loci into transgenic animals, e.g., mice in which the endogenous immunoglobulin genes have been partially or, complete inactivated. Upon challenge, human antibody production is observed, which closely resembles that seen in humans in all respects, including gene rearrangement, assembly and antibody repertoire.

In one embodiment, the antibody is an avian egg yolk antibody. Egg yolks derived from a laying hen are inexpensive and more convenient and can be safer to handle as compared to the hyperimmunized mammalian sera. Also, egg yolk antibodies are able to stand up to the scrutiny under modern animal protection regulations. Immunoglobulin Y (IgY) is an avian immunoglobulin.

The sPLA$_2$-IB peptides are injected into laying fowl, such as hens, preferably at various intervals, to induce an immune response. The hens may be injected intramuscularly or sub-cutaneously. The specific mode of injection is not essential. It is well known that the IgY antibodies produced by the hens in response to such an immunochallenge are transferred and concentrated in the egg yolk.

Once the eggs are harvested, the eggs may be further processed to isolate the egg yolk, which itself may be further processed. The liquid egg yolk may be encapsulated or otherwise used in oral dosage forms. The egg yolk may be dried by spray or refractant drying methods, and the resulting dried powder may be encapsulated or otherwise used in oral dosage forms.

Alternatively, a procedure of partial purification or fractionation may be carried out to remove the majority of the non-aqueous bio-molecules and granules and optionally the majority of other proteins in the egg yolk. Exemplary purification techniques include the use of PEG, dextran sulfate or a natural gum, such as sodium alginate, carrageenan and xanthan gum, to coprecipitate the undesired substances, and the use of an aqueous buffer or water to obtain an aqueous phase rich with antibodies.

In a specific embodiment, the yolk is separated from the egg white, and then washed with distilled water to remove as much albumen as possible. The vitelline membrane encasing the yolk is punctured, and the separated yolk fraction is then diluted with an effective amount of an aqueous buffer or water to form a suspension of the egg yolk. The collected egg yolk may be diluted with an aqueous buffer solution or distilled water in a ratio of about 1:2 to about 1:40 v/v, and more specifically, in a ratio of about 1:5 to about 1:30 v/v. For efficient recovery of yolk antibodies, pH is about 5-7. Desirably, the temperature in this step is within about 0° C. to about 60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

Optionally, the yolk supernatant is further treated with a high concentration of a non-denaturing salt to induce precipitation of the antibodies. Examples of the salts useful for precipitation of the yolk antibodies include, but are not limited to, NaCl, $Na_2SO_4$, $(NH_4)_2SO_4$, KCl, $CaCl_2$, and $MgSO_4$. Specific salts include $Na_2SO_4$ and $(NH_4)_2SO_4$. The salt concentration for precipitating antibodies depends on the type of the salt. In one embodiment, the salt is present in an amount of higher than 15% and lower than 35% by weight, specifically between 20% and 30% by weight of the salt, on the basis of the final volume of the yolk supernatant.

Alternatively, the antibodies may be purified or isolated using any conventional technique such as by immunoaffinity purification.

In one embodiment, egg yolk antibodies are prepared by the following method. Laying hens are inoculated with $sPLA_2$-IB peptide. Optionally, an adjuvant is administered in conjunction with the $sPLA_2$-IB peptide to enhance the immunization. An adjuvant useful for this purpose is a water-in-oil emulsion adjuvant such as complete Freund's adjuvant. The $sPLA_2$-IB peptide causes the hens to produce anti-$sPLA_2$-IB antibodies which are passively transferred into the egg yolk of eggs laid by the hens.

Egg yolks or whole eggs containing the anti-$sPLA_2$-IB antibody can be collected and homogenized to form an emulsion. The resulting emulsion can be dried to form a powder containing the anti-$sPLA_2$-IB antibody. This powder can then be formulated in a manner appropriate to the administration route and then administered to the desired animals using methods known in the art. The preparation is preferably administered orally, such as in an oral dosage form or in a supplement to the animal's diet.

A variety of assays can be used to detect binding of an antibody to $sPLA_2$-IB or a fragment thereof. Representative examples of such assays include: concurrent immunoelectrophoresis, radio-immunoassays, radio-immunoprecipitations, enzyme-linked immunosorbent assays (ELISA), dot blot assays, inhibition or competition assays, and sandwich assays.

In one embodiment, a method of reducing the contribution of the gastrointestinal tract to an inflammatory process comprises orally administering to an individual in need thereof an inhibitor of secretory phospholipase $A_2$-IB. Exemplary inflammatory processes of the gastrointestinal tract include systemic inflammatory response syndromes such as sepsis. In one embodiment, the inhibitor inhibits secretory phospholipase $A_2$-IB without significantly inhibiting TNFα. In a specific embodiment, the inhibitor is an isolated antibody that specifically binds an $sPLA_2$-IB peptide comprising any one of SEQ ID NOs. 1-6. In a more specific embodiment, the inhibitor is an isolated antibody that specifically binds an $sPLA_2$-IB peptide consisting of any one of SEQ ID NOs. 1-6.

In one embodiment, the inhibitor of secretory phospholipase $A_2$-IB is administered as an adjunct to antibiotic therapy. Exemplary antibiotics are those effective in the treatment of bacterial, parasite and/or fungal infections. Examples of antibiotics used to treat sepsis include amikacin, gentamicin, kanamycin, neomycin, netilmicin, streptomycin, tobramycin, loracarbef, ertapenem, cilastatin, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, vancomycin, azithromycin, clarithromycin, dirithromycin, erthromycin, roxithromycin, troleandomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, benzolamide, bumetanide, chlorthalidone, clopamide, dichlorphenamide, ethoxzolamide, indapamide, mafenide, mefruside, metolazone, probenecid, sulfanilamides, sulfamethoxazole, sulfasalazine, sumatriptan, xipamide, democlocycline, doxycycline, minocycline, oxytetracycline, tetracycline, chloramphenical, clindamycin, ethambutol, fosfomycin, fusidic acid, furazolidone, isoniazid, linezolid, metronidazole, mupirocin, nitrofurantoin, platesimycin, pyrazinamide, dalfopristin, rifampin, spectinomycin, telithromycin, and combinations thereof.

In one embodiment, the inhibitor of secretory phospholipase $A_2$-IB is administered within 72 hours of diagnosis of an infection.

The inhibitors of secretory phospholipase $A_2$-IB such as antibodies are administered in the form of an oral composition, such as a pharmaceutical composition or a feed composition. As used herein, "pharmaceutical composition" means therapeutically effective amounts of the inhibitor together with a pharmaceutically acceptable excipient, such as diluents, preservatives, solubilizers, emulsifiers, and adjuvants. As used herein "pharmaceutically acceptable excipients" are well known to those skilled in the art. In a specific embodiment a pharmaceutical composition is a composition suitable for oral administration.

Tablets and capsules for oral administration may be in unit dose form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavoring or coloring agents.

Pharmaceutical compositions may conveniently be presented in unit dosage form and may be prepared by any of the methods well known in the art of pharmacy. The term "unit dosage" or "unit dose" means a predetermined amount of the active ingredient sufficient to be effective for treating an indicated activity or condition. Making each type of pharmaceutical composition includes the step of bringing the active compound into association with a carrier and one or more optional accessory ingredients. In general, the formulations are prepared by uniformly and intimately bringing the active compound into association with a liquid or solid carrier and then, if necessary, shaping the product into the desired unit dosage form.

In one embodiment, an inhibitor of secretory phospholipase $A_2$-IB is administered in a feed or food composition. Food compositions include human and animal food.

The peptides and antibodies disclosed herein are administered to individuals, including mammals such as pigs, cows, dogs and cats, and more specifically humans.

The invention is further illustrated by the following non-limiting examples.

EXAMPLES

Example 1

Mouse $sPLA_2$-IB Peptide Selection, Antibody Production, and ELISA

The sequence for mouse $sPLA_2$-IB was sourced from pubmed.gov protein:

```
NP_035237.1 1
                                       (SEQ ID NO. 8)
           #5                    #2   #3   #4
mklllllaalltaga aahsispra vwqfrnmikct ipgsdplkdynnygc
  #9   #1
ycglggwgtpvd dldrccqthdhcysqa
                  #8
kklesckflidnpytn tysyscsg seitcsaknnkcedficncdreaai
  #10  #6  #7
cfskvpynkeyknldt gkfc.
```

The bolded portions of the sequence are the peptides identified by an antigen prediction program BepiPred. Sequences were then matched with a solved crystal structure (human $sPLA_2$-IB, 3ELO_A) to determine the placement of these sequences and if the peptides would likely be located in the 3-dimensional structure of the $sPLA_2$ molecule such that the peptides were accessible for antibody binding (surface peptides). Ten eight-amino acid-long sequences were then made into peptides by GenScript (Piscatawy N.J.). Five milligrams of peptide(s) were then conjugated to five milligrams bovine gamma globulin or ovalbumin (Sigma Aldrich, St. Louis Mo.) using glutaraldehyde (Fisher Scientific, Pittsburgh Pa.). Peptide-bovine gamma globulin conjugates were then dialyzed against phosphate buffered saline overnight in 6000-8000 molecular weight dialysis membrane tubing (Spectrapor, Los Angeles Calif.). Conjugates were then aliquoted in 1 mg/500 μL aliquots and frozen at −80° C. until ready for injection into the laying hens.

| Sequence # | Sequence | SEQ ID NO: |
|---|---|---|
| #1 | GGWGTPVD | SEQ ID NO. 14 |
| #2 | PGSDPLKD | SEQ ID NO. 15 |
| #3 | KDYNNYGC | SEQ ID NO. 16 |
| #4 | NNYGCYCG | SEQ ID NO. 17 |
| #5 | AAHSISPR | SEQ ID NO. 18 |
| #6 | VPYNKEYK | SEQ ID NO. 1 |
| #7 | KEYKNLDT | SEQ ID NO. 19 |
| #8 | TYSYSCSG | SEQ ID NO. 20 |
| #9 | GCYCGLGG | SEQ ID NO. 21 |
| #10 | CFSKVPYN | SEQ ID NO. 22 |

All procedures involving chickens were approved by the University of Wisconsin, College of Agricultural and Life Sciences Animal Care and Use Committee. Single Comb White Leghorn laying hens were injected (100 μg/chicken) with mouse $sPLA_2$-IB peptide conjugates (3 hens per peptide conjugate) emulsified with Freund's Complete Adjuvant (Fisher Scientific Pittsburgh Pa.). Control antibodies were made by injecting chickens with adjuvant only (FCA antibody or isotype adjuvant control antibody). Chickens were given a booster injection with each peptide (100 mg peptide conjugate/chicken) one week following the initial injection, however the peptide conjugate was emulsified in Freund's Incomplete Adjuvant (Fisher Scientific Pittsburgh Pa.). Eggs were collected beginning three weeks after the initial injection for a period of six weeks. Egg yolks from each peptide were separated from albumen, blended in lots of eggs collected during a 6-week period, lyophilized and stored at room temperature until needed. Enzyme linked immunosorbant assays (ELISAs) were then used to determine the titer of the antibody.

Briefly, 96 well plates were coated with 100 μg of peptide conjugated to ovalbumin dissolved in 12 mL coating buffer (1.59 g $Na_2CO_3$, 2.93 g $NaHCO_3$, 0.2 g $NaN_3$, pH 9.6, 1000 mL total volume) overnight to allow for attachment of the peptide to the nunc MaxiSorp™ F plate (Thermo-Fisher Scientific, Rochester N.Y.). Remaining binding sites on the plates were then blocked with protein free blocking buffer (Pierce, Rockford Ill.) for 1 hour. Plates were then washed 3 times with PBS-0.05% Tween (Fisher-Scientific, Pittsburgh Pa.). The peptide antibody was extracted from dried yolk powder with acidified PBS (pH 4.7) at a concentration of 1:10 (0.2 g yolk powder:1.8 mL acidified PBS) overnight and applied to the plate in 10 fold dilutions from 1:10-1:100,000,000. FCA (adjuvant injected eggs) were used as an isotype control and added to each plate at a 1:10 concentration. Plates were then incubated at room temperature for 1 hour, then washed 5 times as above. Goat anti-chicken secondary antibody (Bethyl Laboratories, Montgomery Tex.) was then added in blocking buffer (5 µL 2° antibody: 12.5 mL blocking buffer) and incubated at room temperature for 30 minutes. Plates were washed 6 times with washing buffer. Substrate was then added in substrate buffer (diethanolamine 97 mL, 100 mg $MgCl_2$, 0.2 g $NaN_3$, 800 mL $ddH_2O$, pH 9.8), incubated for 15 minutes then the plate wells were read at 450 nm with a reference wavelength of 605 nm. Peptide specific antibodies were only used for the study if the peptide specific antibody titer was at least 100 times greater than non-specific binding (defined by the signal of the FCA control antibody).

Example 2

Effect of Anti-$sPLA_2$-IB Antibodies on TNFα Release aOva Technologies uses an anti-$sPLA_2$-IB antibody generated using the intact $sPLA_2$-IB protein to increase growth rates in animals. This antibody was also shown to decrease the amount of TNFα released in LPS stimulated RAW264.7 macrophages. It was therefore hypothesized that anti-$sPLA_2$-IB (whole protein or peptide segments) specific antibodies that inhibit TNF in cell culture would be anti-inflammatory in vivo and reduce sepsis mortality when given orally.

RAW 264.7 cells were grown in DMEM with 10% penicillin and 1% streptomycin (ATCC, Atlanta Ga.). RAW 264.7 cells were purchased from the ATCC (Atlanta Ga.). Cells were revived and propagated 3 generations. Cells were then plated and grown to 70% confluence in 12 well plates (24 hours) prior to the start of the experiment. Egg yolk powder containing antibodies (1, 3-10 and FCA) were plated in triplicate at a concentration of 1:100 in RAW 264.7 growth media. Cells were pretreated with antibodies for 2 hours. Then cells were treated with either 100 ng/well of *E. coli* O55:B5 LPS or saline for 2 hours. Supernatants were then collected for analysis with a commercially available murine-TNFα capture ELISA.

Using TNF as a read-out, 9 antibodies (the chicken would not make antibody to $sPLA_2$-IB peptide #2) were screened in the RAW264.7 macrophage cell line. In three separate experiments we found 5 antibodies (to peptides #4, 5, 8, 9, 10; SEQ ID NOs. 17, 18, 20, 21 and 22) decreased TNFα in the supernatant by at least 50% (FIG. 1). Using this data we set up our first mouse sepsis trial.

Example 3

Effect of Anti-$sPLA_2$-IB Antibodies on Protection of Mice from LPS-Induced Endotoxemia Antibodies that inhibited TNFα production were then tested in a mouse model of sepsis. All procedures involving mice were approved by the University of Wisconsin, College of Agricultural and Life Sciences Animal Care and Use Committee. Balb/c male and female mice aged 5-6 weeks of age were purchased from Harlan (Indianapolis Ind.). Mice were then caged in groups of 3 and randomly assigned a treatment group. In experiment 1: 3 mice were assigned the isotype adjuvant control antibody (FCA) no LPS, all other groups (antibodies FCA with LPS, #'s 4, 5, 8, 9, 10) were assigned 10 mice/group. Mice were then assigned a diet containing 1% egg powder with the desired antibody in feed and allowed to acclimate to the feed for one week. Mice were then gavaged with 100 uL of a 10% solution of the same antibody that was contained in the feed (0.2 g egg powder/1.8 mL acidified PBS pH 4.5), and injected with the $LD_{50}$ of LPS (10 mg/Kg). LPS is *E. coli* O55:B5 (Sigma Aldrich, St. Louis Mo.). In the second experiment mice were not fed any antibody and only gavaged with 100 uL of a 10% solution containing antibodies to peptides #6, 7, 8 (SEQ ID NOs. 1, 19 and 20), aOva (commercial antibody), or FCA at the time of LPS injection. In the third experiment mice were gavaged with 100 uL of a 10% solution containing either 6 or FCA at the time of LPS injection and once every 24 hours thereafter. Mice were monitored at least once every six hours and mortality was recorded.

Figure 2:
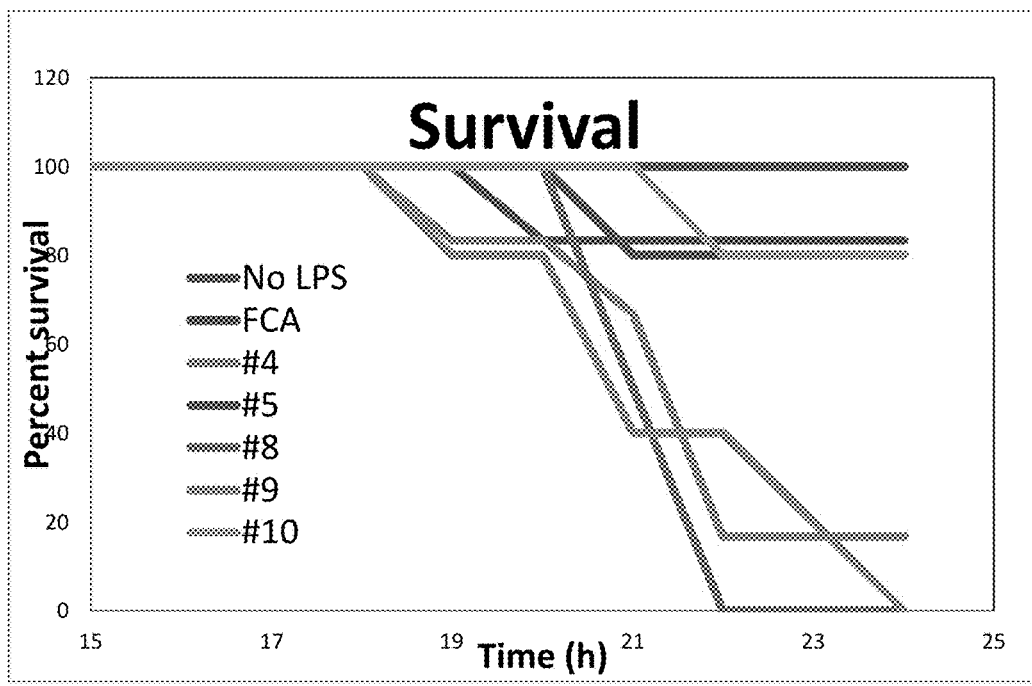
FIG. 2 shows that certain anti-sPLA$_2$-IB antibodies do not protect against sepsis mortality. In this study, Balb/c female mice were divided into groups of 6 and allowed to acclimate to a diet with 1% egg yolk powder with the appropriate antibody for one week. Mice were then gavaged with 100 µl of a 10% solution of egg yolk powder containing the appropriate antibody in acidified PBS immediately before injection with 10 mg/Kg LPS.

Using the data from Example 2, the focus was narrowed to 5 antibodies. In the first experiment mice were fed a diet containing 1% yolk powder containing Freund's Complete Adjuvant (FCA), #4, #5, #8, #9 or #10 peptide (SEQ ID NOs. 17, 18, 20, 21 and 22) specific antibodies for one week. On the day of the experiment, mice were given an oral gavage of 100 uL of a 10% (0.2 g yolk powder containing antibody/1.8 mL acidified PBS) right before injection with the $LD_{50}$ of lipopolysaccharide (LPS) (10 mg/Kg). Mice were then monitored every hour for 24 hours or until the $LD_{50}$ of the Freund's Complete Adjuvant control had been reached. Anti-peptide antibodies with the greatest reduction of TNF production in cell culture increased mortality from approximately 50% to 100% and decreased time to death to less than 22 hours (FIG. 2). The FCA antibody control reduced mortality to only 12% after 24 hours. Thus, the original hypothesis that inhibition of intragastric TNF production by oral administration of anti-$sPLA_2$ antibodies would reduce sepsis mortality was incorrect.

Example 4

Anti-$sPLA_2$-IB Antibodies Inhibit $sPLA_2$-IB Enzyme Function

Since reduction in sepsis mortality associated with feeding the aOva antibody was not related to reductions in TNF and the aOva antibody also inhibits intragastric $sPLA_2$ enzyme activity, $sPLA_2$-IB enzyme function was studied. A fluorescence based $sPLA_2$ activity assay was used to determine if the peptide specific antibodies reduced $sPLA_2$ activity in vitro.

A working solution of $sPLA_2$-IB was freshly prepared by diluting the stock enzyme solution in 0.01 mol/l Tris-HCl buffer (pH 7.4) to a final concentration of 0.04 ng enzyme/µl. The microplate format assay for $sPLA_2$ activity was carried out as follows. BODIPY-labeled 100% PG liposomes (10 µl; 20 µg of phospholipids) were added to 0.01 mol/l Tris-HCl (pH 7.4) containing 10 mmol/l $Ca^{2+}$ in a glass test tube on ice. 20 µL of supernatant from RAW 264.7 cells was added. The buffer volume was adjusted to bring the final reaction mixture volume to 1 ml. To ensure adequate mixing of the liposomes, the test tube was sonicated for 10 seconds prior to the addition of the solution/sample with enzymatic activity. After sonication, the solution/sample was added to the test tube and the reaction mixture was vortexed. Then, 0.3 ml aliquots of the reaction mixtures were promptly transferred in triplicate to the wells of a white polystyrene microplate (Porvair PS White, PerkinElmer, Norwalk, Conn.). The microplate was immediately placed in a temperature controlled (30° C.) microplate reader (PerkinElmer) attached to a Luminescence Spectrometer LS50B (PerkinElmer). The fluorescence intensity (FI) in each well was recorded every 20 s for 90 cycles at 488 nm excitation and 530 nm emission.

To assay $sPLA_2$ activity in the presence of EGTA, 0.01 mol/l Tris-HCl (pH 7.4) containing 10 mmol/l $Ca^{2+}$ and 20 mmol/l EGTA was used as the assay buffer. It should be noted that the frequency and number of FI measurements required to obtain sufficiently representative reaction curves are somewhat dependent on the ability of the spectrophotometer to equilibrate temperature of the reaction mixture and take rapid readings well to well. When determining $sPLA_2$ activity, the first 5 minutes of FI readings were excluded, as temperature of the reaction mixture does not reach equilibrium during this period. The initial FI reading was subtracted from subsequent readings to normalize the reaction curve (plot of FI against time). The reaction curve was fitted to a second-order polynomial equation and the first-degree coefficient was taken to be the initial rate of reaction (V0) and expressed as change in FI/min. The baseline FI change was determined for the reaction in the absence of the enzyme.

Figure 3:
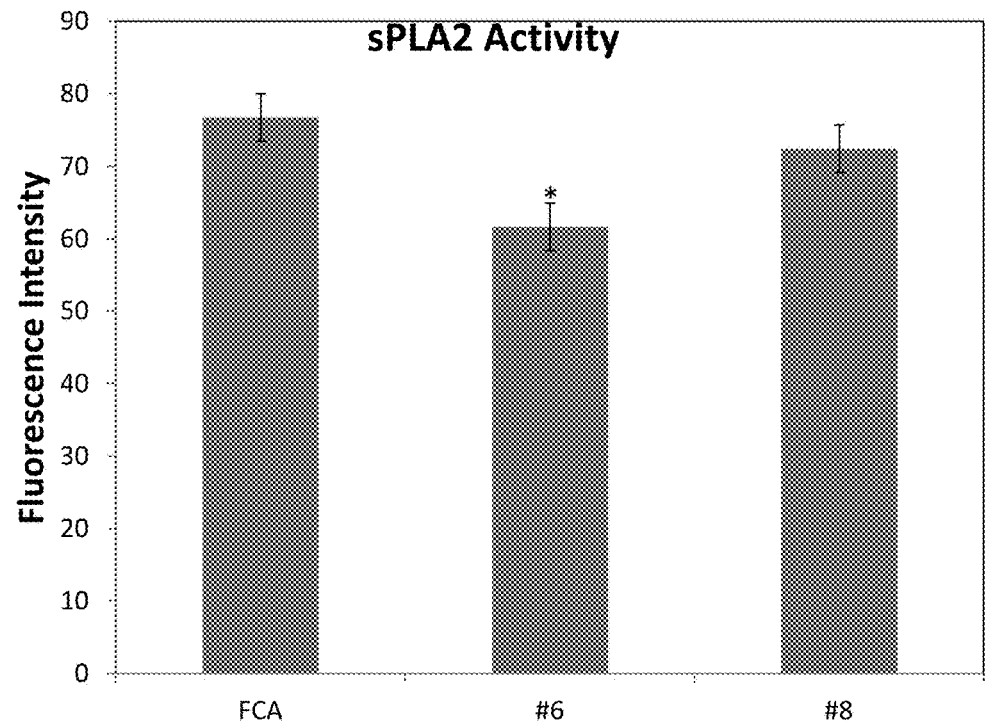
FIG. 3 shows inhibition of sPLA$_2$-IB activity with peptide-specific anti-sPLA2-IB antibodies. sPLA$_2$-IB activity was assayed using a fluorescence based activity assay. Samples from the supernatant of RAW 264.7 cells were used, 20 µL per reaction were needed. * is P<0.05 in a student's t-test.

Previous work demonstrated the aOva antibody inhibits $sPLA_2$ activity in the fluorescence intensity assay. In this assay, antibody to peptide #6 is inhibited $sPLA_2$ activity while antibody to peptide #8 did not (FIG. 3). Other antibodies tested had little effect on $sPLA_2$ activity (data not shown).

Example 5

Figure 4:
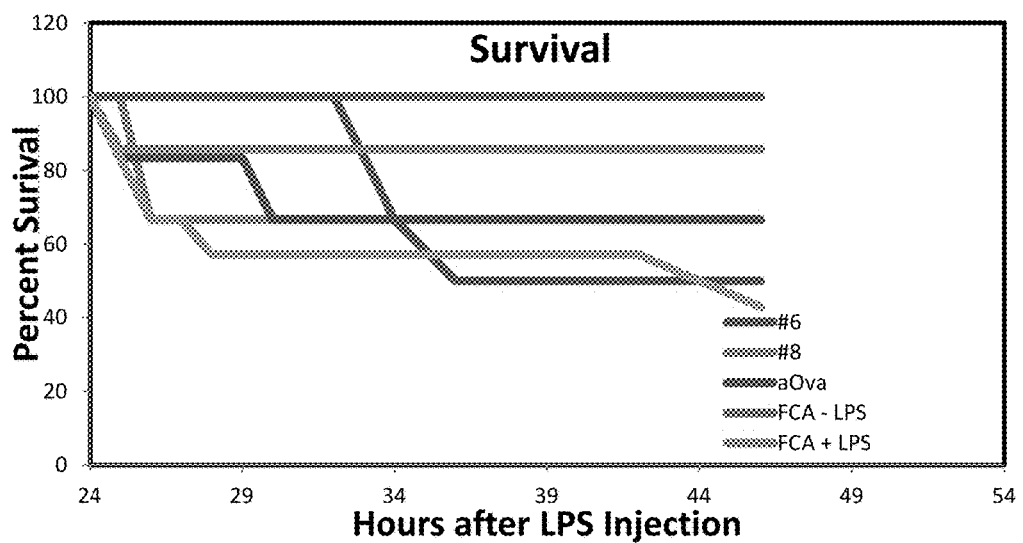
FIG. 4 shows that antibodies that bind sPLA$_2$-IB peptide #6 (SEQ ID NO. 1) are completely protective against sepsis mortality for 29 hours. In this study, Balb/c male mice were gavaged with the appropriate anti-sPLA$_2$ peptide antibody at the time of 10 mg/Kg LPS injection. Groups were isotype adjuvant control antibody (FCA)–LPS (no LPS control), FCA+LPS (isotype control), peptide #8 (SEQ ID NO. 20) antibody (TNF secretion inhibiting antibody), aOva (positive control) and peptide #6 (SEQ ID NO. 1) antibody (test antibody).

Inhibition of $sPLA_2$-IB Enzyme Activity a Better Indicator for in vivo Protection from LPS Induced Mortality Antibody to peptide #6 was then tested in the mouse assay of Example 3. In this experiment, the mice were gavaged at the time of LPS injection since mice did not consume food after LPS injection. Mice were gavaged with anti-peptide #6 antibody, anti-peptide #8 antibody, FCA, a commercial aOva Technologies' antibody, antibodies or with carrier vehicle alone (i.e., no antibody treatment) before LPS injection. In this experiment, it was hypothesized that peptide specific antibodies that inhibited $sPLA_2$ activity would reduce sepsis mortality while antibodies that inhibited TNF secretion would increase mortality. Treatment with anti-peptide #6 antibody reduced sepsis mortality to zero for the first 29 hours of the experiment. The aOva antibody showed an intermediate protection (17% mortality) from sepsis mortality during the first 29 hours. After 29 hours mortality in the anti-peptide #6 antibody and aOva groups was similar to the vehicle treated control (FIG. 4). The rise in morality after 29 hours is consistent with disappearance of antibody from the gastrointestinal tract, leading to the hypothesis that antibody must be present in the GI tract in order to reduce sepsis mortality during this time. Consistent with previous experiments, FCA showed modest protection (15% mortality) from sepsis mortality.

Example 6

Inhibition of $sPLA_2$-IB with Anti-$sPLA_2$-IB #6 is Completely Protective Against Septic Death Based on the hypothesis that antibodies that inhibit $sPLA_2$ activity reduce sepsis mortality, and that antibody must be present during the recovery period, efforts were focused on the anti-peptide #6 antibody in a third mouse experiment. In this experiment, mice were dosed with either anti-peptide #6 or FCA antibody, or vehicle control at the time of LPS injection and once every 24 hours thereafter until mice showed signs of recovery (such as increased movement, decreased piloerection, and increased food consumption). Mice in the vehicle treated group had early sepsis mortality of 30% and a late sepsis mortality of 10% for a 40% total mortality. The FCA treated group had 18% and 27% mortality for the early and late stages of sepsis. Mice orally dosed with anti-peptide #6 antibody daily were completely protected from sepsis mortality for the entire 48 hour duration of the experiment (FIG. 5).

In an experiment using a peritonitis fecal slurry injection, mice given the TNFα inhibiting antibody (#8) all died at 24 hours, no antibody at 31 hours, adjuvant antibody at 36 hours, and no "all death" endpoint was achieved in the mice given the protective antibody (#6). (data not shown) Thus, the antibody that is to a specific peptide VPYNKEYK (SEQ ID NO. 1) on $sPLA_2$-IB inhibits $sPLA_2$-IB enzyme activity. By blocking the enzyme activity of $sPLA_2$-IB, the antibody protects mice against sepsis. This antibody is so specific that movement of just 4 amino acids in either direction makes it ineffective. (#10 (SEQ ID NO. 22) and #7 (SEQ ID NO. 19) comprise four/eight amino acids from #6 yet are ineffective)

The $sPLA_2$-IB inhibitors described herein provide an adjunct to current therapies for sepsis. Current methods to improve the outcome in sepsis include aggressive use of antibiotics, fluid replacement, and anti-inflammatory treatments. However, mortality from severe sepsis remains at 20%, with up to 74% during multi-organ failure. Activated protein C (Drotrecogin Alfa, by Lilly) has shown some promise as an anticoagulant, but it has been shown to cause bleeding and is currently not recommended for sepsis treatment. Previous strategies for treatment of sepsis have all focused on systemic processes in inflammation. The $sPLA_2$-IB inhibitors described herein target inflammation in the gastrointestinal tract. Key to the approach is to disconnect the feed-forward loop of inflammation that involves the luminal contents of the gastrointestinal tract. In animal models it has been shown that when the gastrointestinal tract is sterile (germ-free), animals are resistant to septic shock induced by systemically applied LPS. By targeting the key mediator that results in a breakdown in barrier function in the gastrointestinal system, the role of the gastrointestinal tract as a feed forward loop in driving sepsis to shock can be reduced.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A feed or a food composition comprising an isolated antibody that specifically binds secretory phospholipase $A_2$-IB, wherein the isolated antibody specifically binds a peptide (V/A/R)PYNK(A/E)(H/Y)K (SEQ ID NO. 6).

2. The feed or a food composition of claim 1, wherein the peptide comprises 8 to 38 contiguous amino acids of the secretory phospholipase $A_2$-IB.

3. The feed or a food composition of claim 1, wherein the peptide comprises a sequence selected from VPYNKEYK (SEQ ID NO. 1), APYNKAHK(SEQ ID NO. 2), APYNKEHK (SEQ ID NO. 3), RPYNKEYK (SQ ID NO. 4), and VPYNKEHK (SEQ ID NO. 5).

4. The feed or a food composition of claim 1, wherein the isolated antibody is a polyclonal antibody, a monoclonal antibody, a humanized antibody, or an avian egg yolk antibody.

5. The feed or a food composition of claim 1, in the form of a human food composition.

6. The feed or a food composition of claim 1, in the form of an animal feed composition.

7. The feed or a food composition of claim 1, wherein the antibody is an avian egg yolk antibody.

8. An oral, solid pharmaceutical composition comprising a pharmaceutically acceptable excipient and isolated antibody that specifically binds secretory phospholipase $A_2$-IB, wherein the isolated antibody specifically binds a peptide (V/A/R)PYNK(A/E)(H/Y)K (SEQ ID NO. 6).

9. The oral, solid pharmaceutical dosage form of claim 8, wherein the isolated antibody is a polyclonal antibody, a monoclonal antibody, a humanized antibody, or an avian egg yolk antibody.

10. The oral, solid pharmaceutical dosage form of claim 8, wherein the isolated antibody is an avian egg yolk antibody.

* * * * *